United States Patent
Bathe et al.

(10) Patent No.: US 6,890,744 B2
(45) Date of Patent: May 10, 2005

(54) METHODS FOR PRODUCING AMINO ACIDS IN CORYNEFORM BACTERIA USING AN ENHANCED SIGD GENE

(75) Inventors: Brigitte Bathe, Salzkotten (DE); Caroline Kreutzer, Melle (DE); Monika Martens, Bielefeld (DE); Mike Farwick, Bielefeld (DE); Thomas Hermann, Bielefeld (DE); Walter Pfefferle, Halle (DE)

(73) Assignee: Degussa AG, Düsseldorf (DE)

( * ) Notice: Subject to any disclaimer, the term of this patent is extended or adjusted under 35 U.S.C. 154(b) by 227 days.

(21) Appl. No.: 09/941,945

(22) Filed: Aug. 30, 2001

(65) Prior Publication Data

US 2002/0111468 A1 Aug. 15, 2002

(30) Foreign Application Priority Data

Sep. 2, 2000 (DE) .......................................... 100 43 331

(51) Int. Cl.[7] .............................................. C12P 13/04
(52) U.S. Cl. ...................................... 435/106; 435/115
(58) Field of Search .................................. 435/106, 115

(56) References Cited

U.S. PATENT DOCUMENTS

2002/0197605 A1 * 12/2002 Nakagawa et al. ............ 435/6

FOREIGN PATENT DOCUMENTS

| EP | 0864654 A1 | * | 9/1998 |
| EP | 0 864 654 | | 9/1998 |
| EP | 1 108 790 A2 | | 6/2001 |
| JP | 2002/191370 | * | 7/2002 |
| WO | WO 96/38478 | | 12/1996 |
| WO | WO 98/31789 | | 7/1998 |

OTHER PUBLICATIONS

Edward A. Birge "Bacterial and bacteriophage Genetics", Third Edition, pp. 69–70 (date not indicated).
Rolf Knippers "Molekular Genetik", 1995, Georg Thieme Verlag, Stuttgart—New York, p. 67.
AX127441 Sequence 7060 from Patent EP 1108790, dated May 10, 2001.
P10726, dated Feb., 1996.
Caramori T et al., "Role of FlgM in sigmaD–dependant gene expression in *bacillus subtilis*", Journal of Bacteriology, Jun. 1996, vol. 178, No. 11, pp. 3113–3118.
Oguiza J et al., "Multiple Sigma Factor Genes in *Brevibacterium Lactofermentum*: Characterization of sigA and sigB", Journal of Bacteriology, Jan. 1996, vol. 178, No. 2, pp. 550–553.

* cited by examiner

*Primary Examiner*—Kathleen Kerr
(74) *Attorney, Agent, or Firm*—Smith, Gambrell & Russell

(57) ABSTRACT

The invention relates to an isolated polynucleotide from *Corynebacterium glutamicum* having a polynucleotide sequence which codes for the sigD gene, and a host-vector system having a coryneform host bacterium in which the sigD gene is present in enhanced form and a vector which carries at least the sigD gene according to SEQ ID No: 1, and the use of polynucleotides which comprise the sequences according to the invention as hybridization probes.

18 Claims, No Drawings

SEQUENCE LISTING

<160> NUMBER OF SEQ ID NOS: 2

<210> SEQ ID NO 1
<211> LENGTH: 1129
<212> TYPE: DNA
<213> ORGANISM: Corynebacterium glutamicum
<220> FEATURE:
<221> NAME/KEY: CDS
<222> LOCATION: (301)..(864)
<223> OTHER INFORMATION:

<400> SEQUENCE: 1

```
catatgcagg cgaactcctg ctagtacgcc cgttctgacc tgcggttatg tgtcgaggtg      60
aatctccggt gaattcttat agataacttg tttttgcagg tcaggacggg gttaagggga     120
tgggtgttat ctgtcagtat gtgaggagat caaggtgttg ggggttctag ttgctaagat     180
ggtgaaaacc cgtgaggcca aaatccaact gggtgaatta cccctgcata aatgcatgag     240
ggctttatac ttgtcttatt attaaacttt tagggttttg atgcaggaag gtgcgagaac     300
```

```
ttg gct gat act gag cgc gag ctc gct gac ctg gta ccg cag gca acg     348
Met Ala Asp Thr Glu Arg Glu Leu Ala Asp Leu Val Pro Gln Ala Thr
 1               5                  10                  15 gcg ggc gat cgt cgg gca ttg caa aga ata atg gag att att cac ccc     396
Ala Gly Asp Arg Arg Ala Leu Gln Arg Ile Met Glu Ile Ile His Pro
             20                  25                  30 att gtt ttg cgt tat gct cgc gct cgt att gga ggt gga cgc cag cca     444
Ile Val Leu Arg Tyr Ala Arg Ala Arg Ile Gly Gly Gly Arg Gln Pro
         35                  40                  45 acg gca gaa gac gtt gct caa gaa atc tgc ctg gcg gta gcc acc tcc     492
Thr Ala Glu Asp Val Ala Gln Glu Ile Cys Leu Ala Val Ala Thr Ser
 50                  55                  60 att agg aac ttt gtc gac cag ggt agg ccg ttc atg gcg ttt gtc tac     540
Ile Arg Asn Phe Val Asp Gln Gly Arg Pro Phe Met Ala Phe Val Tyr
 65                  70                  75                  80 ggc att gca tct aac aag gtc gca gat gct cac agg gcg atg tcg agg     588
Gly Ile Ala Ser Asn Lys Val Ala Asp Ala His Arg Ala Met Ser Arg
                 85                  90                  95 gat aaa tcg act cct att gag gaa gtc cca gaa act tca cca gat act     636
Asp Lys Ser Thr Pro Ile Glu Glu Val Pro Glu Thr Ser Pro Asp Thr
            100                 105                 110 ttt acc ccc gaa gac ttt gcg ctg gtc agc gat gga agt aac aga gtt     684
Phe Thr Pro Glu Asp Phe Ala Leu Val Ser Asp Gly Ser Asn Arg Val
        115                 120                 125 agg gaa ctt ctc gat cta ctg agt gaa aag gca cgc gac att ctt atc     732
Arg Glu Leu Leu Asp Leu Leu Ser Glu Lys Ala Arg Asp Ile Leu Ile
    130                 135                 140 ttg aga gtt atc gtt ggt ctt tcc gca gaa gaa act gca gag atg gtg     780
Leu Arg Val Ile Val Gly Leu Ser Ala Glu Glu Thr Ala Glu Met Val
145                 150                 155                 160 ggc agc acc cca ggt gct gta cga gtt gcc caa cac agg gca ctc acg     828
Gly Ser Thr Pro Gly Ala Val Arg Val Ala Gln His Arg Ala Leu Thr
                165                 170                 175 aca ctt cga agc aca ctt gag cag cag gag aac aag taatgactcg          874
Thr Leu Arg Ser Thr Leu Glu Gln Gln Glu Asn Lys
            180                 185
```

```
acgtctacat ggtggtgagc aggatggcca ggaacacgtt aaaggacagc taaagcagct     934
gttcgacgac gacgcgttct tgactgacct gtcccgcggc gttgatccct cagagggcga     994
tgacgccctc gctggcctcc tcctcgattt aacaaaggaa gctcaggagc cgccggcaac    1054
```

```
aatgccggat tggtctactt tgctccctgg aattttggat caggatcagg atttgccagt    1114
ggaatccact tcgga                                                      1129
```

<210> SEQ ID NO 2
<211> LENGTH: 188
<212> TYPE: PRT
<213> ORGANISM: Corynebacterium glutamicum

<400> SEQUENCE: 2

```
Met Ala Asp Thr Glu Arg Glu Leu Ala Asp Leu Val Pro Gln Ala Thr
1               5                   10                  15

Ala Gly Asp Arg Arg Ala Leu Gln Arg Ile Met Glu Ile Ile His Pro
            20                  25                  30

Ile Val Leu Arg Tyr Ala Arg Ala Arg Ile Gly Gly Gly Arg Gln Pro
        35                  40                  45

Thr Ala Glu Asp Val Ala Gln Glu Ile Cys Leu Ala Val Ala Thr Ser
    50                  55                  60

Ile Arg Asn Phe Val Asp Gln Gly Arg Pro Phe Met Ala Phe Val Tyr
65                  70                  75                  80

Gly Ile Ala Ser Asn Lys Val Ala Asp Ala His Arg Ala Met Ser Arg
                85                  90                  95

Asp Lys Ser Thr Pro Ile Glu Glu Val Pro Glu Thr Ser Pro Asp Thr
            100                 105                 110

Phe Thr Pro Glu Asp Phe Ala Leu Val Ser Asp Gly Ser Asn Arg Val
        115                 120                 125

Arg Glu Leu Leu Asp Leu Leu Ser Glu Lys Ala Arg Asp Ile Leu Ile
    130                 135                 140

Leu Arg Val Ile Val Gly Leu Ser Ala Glu Glu Thr Ala Glu Met Val
145                 150                 155                 160

Gly Ser Thr Pro Gly Ala Val Arg Val Ala Gln His Arg Ala Leu Thr
                165                 170                 175

Thr Leu Arg Ser Thr Leu Glu Gln Gln Glu Asn Lys
            180                 185
```

METHODS FOR PRODUCING AMINO ACIDS IN CORYNEFORM BACTERIA USING AN ENHANCED SIGD GENE

BACKGROUND OF THE INVENTION

The present invention provides nucleotide sequences of coryneform bacteria coding for the sigD gene and a process for the enzymatic production of amino acids using bacteria in which the sigD gene is enhanced. All references cited herein are expressly incorporated by reference. Incorporation by reference is also designated by the term "I.B.R." following any citation.

L-amino acids are used in human medicine and in the pharmaceutical industry, in the foodstuffs industry and, most especially, in animal nutrition.

It is known that amino acids can be produced by fermentation of strains of coryneform bacteria, in particular *Corynebacterium glutamicum*. On account of the great importance of amino acids efforts are constantly being made to improve the production processes. Process improvements may involve fermentation technology measures such as for example stirring and provision of oxygen, or the composition of the nutrient media, such as for example the sugar concentration during the fermentation, or the working-up to the product form by for example ion exchange chromatography or the intrinsic performance properties of the microorganism itself.

In order to improve the performance properties of these microorganisms methods involving mutagenesis, selection and mutant selection are employed. In this way strains are obtained that are resistant to antimetabolites or are auxotrophic for regulatorily important metabolites, and that produce amino acids.

For some years methods of recombinant DNA technology have also been used to improve L-amino acid-producing strains of corynebacterium, by amplifying individual amino acid biosynthesis genes and investigating the effect on amino acid production.

The invention provides new techniques for the improved enzymatic production of amino acids.

BRIEF SUMMARY OF THE INVENTION

When L-amino acids or amino acids are mentioned hereinafter, it is understood that this refers to one or more amino acids including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Lysine is particularly preferred.

The present invention provides an isolated polynucleotide from coryneform bacteria containing a polynucleotide sequence coding for the sigD gene, selected from the group
a) polynucleotide that is at least 70% identical to a polynucleotide coding for a polypeptide that contains the amino acid sequence of SEQ ID No. 2,
b) polynucleotide coding for a polypeptide that contains an amino acid sequence that is at least 70% identical to the amino acid sequence of SEQ ID No. 2,
c) polynucleotide that is complementary to the polynucleotides of a) or b), and
d) polynucleotide containing at least at least 15 successive nucleotides of the polynucleotide sequence of a), b) or c),
the polypeptide preferably having the activity of the sigma factor D.

The present invention also provides the aforementioned polynucleotide, which is preferably a replicable DNA containing:
(i) the nucleotide sequence shown in SEQ ID No. 1, or
(ii) at least one sequence that corresponds to the sequence (i) within the region of degeneracy of the genetic code, or
(iii) at least one sequence that hybridizes with the sequence that is complementary to the sequence (i) or (ii), and optionally
(iv) functionally neutral sense mutations in (i).

The invention furthermore provides
a replicable polynucleotide, in particular DNA, containing the nucleotide sequence as shown in SEQ ID No. 1;
a polynucleotide coding for a polypeptide that contains the amino acid sequence as shown in SEQ ID No. 2;
a vector containing the polynucleotide according to the invention, in particular a shuttle vector or plasmid vector, and
coryneform bacteria that contain the vector or in which the sigD gene is enhanced.

The present invention moreover provides polynucleotides that consist substantially of a polynucleotide sequence that can be obtained by screening by means of hybridization of a corresponding gene library of a coryneform bacterium that contains the complete gene or parts thereof, with a probe that contains the sequence of the polynucleotide of the invention according to SEQ ID No. 1 or a fragment thereof, and isolation of the aforementioned polynucleotide sequence.

DETAILED DESCRIPTION OF THE INVENTION

Polynucleotides that contain the sequences according to the invention are suitable as hybridization probes for RNA, cDNA and DNA in order to isolate nucleic acids or polynucleotides or genes in their full length that code for the sigma factor D, or to isolate such nucleic acids or polynucleotides or genes that have a high sequence similarity to that of the sigD genes. They are also suitable for incorporation into so-called "arrays", "micro arrays" or "DNA chips" in order to detect and determine the corresponding polynucleotides.

Polynucleotides that contain the sequences according to the invention are furthermore suitable as primers with the aid of which, and by employing the polymerase chain reaction (PCR), DNA of genes can be produced that code for the sigma factor D.

Such oligonucleotides which serve as probes or primers comprise at least 25, 26, 27, 28, 29 or 30, preferably at least 20, 21, 22, 23 or 24 very particularly preferably at least 15, 16, 17, 18 or 19 successive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" denotes separated from its natural environment.

"Polynucleotide" refers in general to polyribonucleotides and polydeoxyribonucleotides, which may be unmodified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

The term "polypeptides" is understood to mean peptides or proteins that contain two or more amino acids bound by peptide bonds.

The polypeptides according to the invention include a polypeptide according to SEQ ID No. 2, in particular those with the biological activity of the sigma factor D and also those which are at least 70% to 80%, preferably at least 81% to 85%, particularly preferably at least 91%, 93%, 95%, 97% or 99% identical to the polypeptide according to SEQ ID No. 2 and have the activity mentioned.

The invention furthermore provides a process for the enzymatic production of amino acids selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using coryneform bacteria that in particular already produce amino acids and in which the nucleotide sequences coding for the sigD gene are enhanced, in particular overexpressed.

The term "enhancement" describes in this connection the raising of the intracellular activity of one or more enzymes in a microorganism that are coded by the corresponding DNA, by for example increasing the number of copies of the gene or genes, using a strong promoter, or using a gene that codes for a corresponding enzyme having a high activity, and optionally combining these measures.

The microorganisms that are the subject of the present invention are able to produce L-amino acids from glucose, sucrose, lactose, fructose, maltose, molasses, starch, cellulose or from glycerol and ethanol. The microorganisms may be representatives of coryneform bacteria, in particular of the genus *Corynebacterium*. In the genus *Corynebacterium* there should in particular be mentioned the species *Corynebacterium glutamicum*, which is known to those skilled in the art for its ability to produce L-amino acids.

Suitable strains of the genus *Corynebacterium*, in particular of the species *Corynebacterium glutamicum* (*C. glutamicum*), are in particular the known wild type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-amino acid-producing mutants or strains produced therefrom.

The inventors have successfully isolated from *C. glutamicum* the new sigD gene coding for the enzyme sigma factor D.

In order to isolate the sigD gene or also other genes from *C. glutamicum*, a gene library of this microorganism is first of all incorporated in *Escherichia coli* (*E. coli*). The incorporation of gene libraries is described in generally known textbooks and manuals. As examples there may be mentioned the textbook by Winnacker: Gene and Klone, Eine Einführung in die Gentechnologie (Verlag Chemie, Weinheim, Germany, 1990) I.B.R. or the manual by Sambrook et al.: Molecular Cloning, A Laboratory Manual (Cold Spring Harbor Laboratory Press, 1989) I.B.R. A very well-known gene library is that of the *E. coli* K-12 strain W3110, which was incorporated by Kohara et al. (Cell 50, 495–508 (1987)) I.B.R. into λ vectors. Bathe et al. (Molecular and General genetics, 252:255–265, 1996) I.B.R. describe a gene library of *C. glutamicum* ATCC13032 that has been incorporated by means of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.).

Börmann et al. (Molecular Microbiology 6(3), 317–326) (1992)) I.B.R. in turn describe a gene library of *C. glutamicum* ATCC13032 using the cosmid pHC79 (Hohn and Collins, Gene 11, 291–298 (1980) I.B.R.).

In order to produce a gene library of *C. glutamicum* in *E. coli*, there may also be used plasmids such as pBR322 (Bolivar, Life Sciences, 25, 807–818 (1979) I.B.R.) or pUC9 (Vieira et al., 1982, Gene, 19:259–268 I.B.R.). Suitable hosts are in particular those *E. coli* strains that are restriction-defective and recombinant-defective. An example of such is the strain DH5αmcr, which has been described by Grant et al. (Proceedings of the National Academy of Sciences USA, 87 (1990) 4645–4649) I.B.R. The long DNA fragments cloned with the aid of cosmids can in turn then be subcloned into common vectors suitable for the sequencing and subsequently sequenced, as is described for example by Sanger et al. (Proceedings of the National Academy of Sciences of the United States of America, 74:5463–5467, 1977) I.B.R.

The DNA sequences obtained can then be investigated using known algorithms or sequence analysis programs, such as for example that of Staden (Nucleic Acids Research 14, 217–232(1986)) I.B.R., that of Marck (Nucleic Acids Research 16, 1829–1836 (1988)) I.B.R. or the GCG program of Butler (Methods of Biochemical Analysis 39, 74–97 (1998)) I.B.R.

The new DNA sequence of *C. glutamicum* coding for the sigD gene was obtained in this way, and as SEQ ID No. 1 is part of the present invention. The amino acid sequence of the corresponding protein was also derived from the existing DNA sequence using the aforedescribed methods. The resultant amino acid sequence of the sigD gene product is shown in SEQ ID No. 2.

Coding DNA sequences that result from SEQ ID No. 1 due to the degeneracy of the genetic code are likewise covered by the present invention. Similarly, DNA sequences that hybridize with SEQ ID No. 1 or parts of SEQ ID No. 1 are also part of the invention. In the specialist field conservative amino acid replacements, such as for example the replacement of glycine by alanine or of aspartic acid by glutamic acid, in proteins are furthermore known as sense mutations that do not lead to any basic change in the activity of the protein, i.e. are functionally neutral. It is furthermore known that changes at the N-end and/or C-end of a protein do not significantly impair their function or indeed may even stabilize their function. The person skilled in the art can find relevant information on this in, inter alia, Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks and manuals on genetics and molecular biology. Amino acid sequences that are obtained in a corresponding manner from SEQ ID No. 2 are likewise covered by the invention.

In the same way, DNA sequences that hybridize with SEQ ID No. 1 or parts of SEQ ID No. 1 are also covered by the invention. Finally, DNA sequences that are produced by the polymerase chain reaction (PCR) using primers resulting from SEQ ID No. 1, are also part of the invention. Such oligonucleotides typically have a length of at least 15 nucleotides.

The person skilled in the art can find information on the identification of DNA sequences by means of hybridization in, inter alia, the manual "The DIG System User's Guide for Filter Hybridization" published by Boehringer Mannheim GmbH (Mannheim, Germany, 1993) I.B.R. and in Liebl et al. (International Journal of Systematic Bacteriology (1991) 41: 255–260) I.B.R. The hybridization takes place under strict conditions, in other words only hybrids are formed in which the probe and target sequence, i.e. the polynucleotides treated with the probe, are at least 70% identical. It is known that the strictness of the hybridization conditions including the washing step is influenced or determined by varying the buffer composition, temperature and the salt concentration. The hybridization reaction is preferably carried out under conditions that are relatively less strict compared to the wash steps (Hybaid Hybridisation Guide, Hybaid Limited, Teddington, UK, 1996 I.B.R.)

For the Hybridisation reaction there may for example be used a 5×SSC buffer at a temperature of ca. 50–68° C. In this connection probes can also hybridize with polynucleotides that are less than 70% identical to the probe sequence. Such hybrids are less stable and are removed by washing under stringent conditions. This may be achieved for example by reducing the salt concentration to 2×SSC and then if necessary to 0.5×SSC (The DIG System User's Guide for Filter Hybridisation, Boehringer Mannheim, Mannheim, Germany, 1995 I.B.R.), a temperature of ca. 50–68° C. being established. It is also possible to reduce the salt concentration down to 0.1×SSC. By stepwise raising of the Hybridisation temperature in steps of ca. 1–2° C. from 50 to 68° C., polynucleotide fragments can be isolated that are for example at least 70% or at least 80% or even at least 90% to 95% identical to the sequence of the probe that is used. Further details relating to Hybridisation may be obtained in the form of so-called kits available on the market (e.g. DIG Easy Hyb from Roche Diagnostics GmbH, Mannheim, Germany, Catalog No. 1603558 I.B.R.).

The person skilled in the art can find details on the amplification of DNA sequences by means of the polymerase chain reaction (PCR) in, inter alia, the manual by Gait: Oligonucleotides Synthesis: A Practical Approach (IRL Press, Oxford, UK, 1984) I.B.R. and in Newton and Graham: PCR (Spektrum Akademischer Verlag, Heidelberg, Germany, 1994) I.B.R.

In the course of work carried out in connection with the present invention it was established that coryneform bacteria after overexpression of the sigD gene produce amino acids in an improved manner.

In order to achieve an overexpression the number of copies of the corresponding genes can be increased, or alternatively the promoter and regulation region or the ribosome binding site located upstream of the structure gene can be mutated. Expression cassettes that are incorporated upstream of the structure gene act in the same way. By means of inducible promoters it is in addition possible to increase the expression in the course of the enzymatic amino acid production. The expression is similarly improved by measures aimed at prolonging the lifetime of the m-RNA. Furthermore, the enzyme activity is also enhanced by preventing the degradation of the enzyme protein. The genes or gene constructs may either be present in plasmids having different numbers of copies, or may be integrated and amplified in the chromosome. Alternatively, an overexpression of the relevant genes may furthermore be achieved by altering the composition of the media and the culture conditions.

The person skilled in the art can find details on the above in, inter alia, Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in European Patent Specification 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in Patent Application WO 96/15246 I.B.R., in Malumbres et al. (Gene 134, 15–24 (1993)) I.B.R., in Japanese laid open Specification JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks on genetics and molecular biology.

For the enhancement the sigD gene according to the invention was overexpressed for example by means of episomal plasmids. Suitable plasmids are those that are replicated in coryneform bacteria. Numerous known plasmid vectors, such as for example pZ1 (Menkel et al., Applied and Environmental Microbiology (1989) 64: 549–554 I.B.R.), pEKEx1 (Eikmanns et al., Gene 102:93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as for example those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.) may be used in a similar way.

Furthermore, also suitable are those plasmid vectors with the aid of which the process of gene amplification by integration in the chromosome can be employed, such as has been described for example by Reinscheid et al. (Applied and Environmental Microbiology 60, 126–132 (1994) I.B.R.) for the duplication and amplification of the hom-thrB operon. In this method the complete gene is cloned into a plasmid vector that can replicate in a host (typically *E. coli*) but not in *C. glutamicum*. Suitable vectors are for example pSUP301 (Simon et al., Bio/Technology 1, 784–791 (1983) I.B.R.), pK18mob or pK19 mob (Schäfer et al., Gene 145, 69–73 (1994) I.B.R.), pGEM-T (Promega Corporation, Madison, Wis., USA), pCR2.1-TOPO (Shuman (1994). Journal of Biological Chemistry 269:32678-84 I.B.R.; U.S. Pat. No. 5,487,993 I.B.R.), pCR®Blunt (Invitrogen, Groningen, Netherlands; Bernard et al., Journal of Molecular Biology, 234: 534–541 (1993) I.B.R.), pEM1 (Schrumpf et al, 1991, Journal of Bacteriology 173:4510–4516 I.B.R.) or pBGS8 (Spratt et al., 1986, Gene 41: 337–342 I.B.R.). The plasmid vector that contains the gene to be amplified is then transferred by conjugation or transformation into the desired strain of *C. glutamicum*. The method of conjugation is described for example in Schäfer et al. (Applied and Environmental Microbiology 60, 756–759 (1994) I.B.R.). Transformation methods are described for example in Thierbach et al. (Applied Microbiology and Biotechnology 29, 356–362 (1988) I.B.R.), Dunican and Shivnan (Bio/Technology 7, 1067–1070 (1989) I.B.R.) and Tauch et al. (FEMS Microbiological Letters 123, 343–347 (1994) I.B.R.). After homologous recombination by means of a crossover event, the resulting strain contains at least two copies of the relevant gene.

In addition it may be advantageous for the production of L-amino acids to enhance, in particular to overexpress, in addition to the sigD gene also one or more enzymes of the respective biosynthesis pathway, glycolysis, anaplerosis, citric acid cycle, pentose phosphate cycle, amino acid export and optionally regulatory proteins.

Thus for example, for the production of L-amino acids, in addition to the enhancement of the sigD gene one or more genes selected from the following group may be enhanced, in particular overexpressed:

the gene dapA coding for dihydrodipicolinate synthase (EP-B 0 197 335 I.B.R.), the gene gap coding for glyceraldehyde-3-phosphate dehydrogenase (Eikmanns (1992), Journal of Bacteriology 174:6076–6086 I.B.R.), the gene tpi coding for triosephosphate isomerase (Eikmanns (1992), Journal of Bacteriology 174:6076–6086 I.B.R.), the gene pgk coding for 3-phosphoglycerate kinase (Eikmanns (1992), Journal of Bacteriology 174:6076–6086 I.B.R.), the gene zwf coding for glucose-6-phosphate dehydrogenase (JP-A-09224661 I.B.R.), the gene pyc coding for pyruvate carboxylase (DE-A-198 31 609 I.B.R.), the gene mqo coding for malate-quinone-oxidoreductase (Molenaar et al., European Journal of Biochemistry 254, 395–403 (1998) I.B.R.), the gene lysC coding for a feedback-resistant aspartate kinase (Accession No. P26512), the gene lysE coding for lysine export (DE-A-195 48 222 I.B.R.), the gene hom coding for homoserine dehydrogenase (EP-A 0131171 I.B.R.), the gene ilvA coding for threonine dehydratase (Möckel et al., Journal of Bacteriology (1992) 8065–8072) I.B.R.) or the allele ilvA(Fbr) coding for a feedback-resistant threonine dehydratase (Möckel et al., (1994) Molecular Microbiology 13: 833–842 I.B.R.), the gene ilvBN coding for acetohydroxy acid synthase (EP-B 0356739 I.B.R.), the gene ilvD coding for dihydroxy acid dehydratase (Sahm and Eggeling (1999) Applied and Environmental Microbiology 65: 1973–1979 I.B.R.), the gene zwal coding for the Zwal protein (DE: 19959328.0 I.B.R., DSM 13115).

Furthermore, it may be advantageous for the production of L-an no acids, in addition to the enhancement of the sigD genes also to attenuate, in particular to reduce, the expression of one or more genes selected from the group the gene pck coding for phosphoenol pyruvate carboxykinase (DE 199 50 409.1 I.B.R.; DSM 13047), the gene pgi coding for glucose-6-phosphate isomerase (U.S. Pat. No. 6,586,214 I.B.R.; DSM 12969), the gene poxB coding for pyruvate oxidase (DE: 1995 1975.7 I.B.R.; DSM 13114), the gene zwa2 coding for the Zwa2 protein (DE: 19959327.2 I.B.R., DSM 13113).

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

In addition it may be advantageous for the production of amino acids, in addition to the overexpression of the sigD gene also to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982 I.B.R.).

The microorganisms produced according to the invention are likewise the subject of the invention and may be cultivated continuously or batchwise in a batch process (batch cultivation) or in a fed batch process (feed process) or repeated fed batch process (repetitive feed process) for the purposes of production of amino acids. A summary of know cultivation methods is given in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Brunswick/Wiesbaden, 1994) I.B.R.).

The culture medium to be used must suitably satisfy the requirements of the relevant strains. Descriptions of culture media for various microorganisms are given in the manual "Manual of Methods for General Bacteriology" of the American Society for Bacteriology (Washington D.C., USA, 1981) I.B.R.

Carbon sources that may be used include sugars and carbohydrates such as for example glucose, sucrose, lactose, fructose, maltose, molasses, starch and cellulose, oils and fats such as for example soya bean oil, sunflower oil, peanut oil and coconut oil, fatty acids such as for example palmitic acid, stearic acid and linoleic acid, alcohols such as for example glycerol and ethanol, and organic acids such as for example acetic acid. These substances may be used individually or as a mixture.

Nitrogen sources that may be used include organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture.

Phosphorus sources that may be used include phosphoric acid, potassium dihydrogen phosphate or dipotassium hydrogen phosphate or the corresponding sodium salts. The culture medium must furthermore contain salts of metals, such as for example magnesium sulfate or iron sulfate, that are necessary for growth. Finally, essential growth promoters such as amino acids and vitamins may be used in addition to the aforementioned substances. Suitable precursors may furthermore be added to the culture medium. The aforementioned starting substances may be added to the culture in the form of a single one-off batch, or may be suitably metered in during the culture process.

Basic compounds such as sodium hydroxide, potassium hydroxide, ammonia or ammonia water, or acidic compounds such as phosphoric acid or sulfuric acid, are used in a suitable manner in order to control the pH of the culture. Anti-foaming agents such as for example fatty acid polyglycol esters may be used to control foam formation. In order to maintain the stability of plasmids suitable selectively acting substances such as for example antibiotics may be added to the medium. In order to maintain aerobic conditions, oxygen or oxygen-containing gas mixtures such as for example air are introduced into the culture. The temperature of the culture is normally 20° C. to 45° C. and preferably 25° C. to 40° C. The culture is continued until a maximum of the desired product has been formed. This objective is normally achieved within 10 hours to 160 hours.

Methods for the determination of L-amino acids are known to the person skilled in the art. The analysis may be carried out for example as described by Spackman et al. (Analytical Chemistry, 30, (1958), 1190) I.B.R. by ion exchange chromatography followed by ninhydrin derivation, or can be carried out by reversed phase HPLC, as described by Lindroth et al. (Analytical Chemistry (1979) 51: 1167–1174) I.B.R.

The process according to the invention serves for the enzymatic production of amino acids.

The present invention is described in more detail hereinafter with the aid of examples of implementation.

The isolation of plasmid DNA from *Escherichia coli* as well as all techniques involved in restriction, Klenow treatment and alkaline phosphatase treatment have been carried out by Sambrook et al. (Molecular Cloning. A Laboratory Manual (1989) Cold Spring Harbor Laboratory Press, Cold Spring Harbor, N.Y., USA) I.B.R. Methods for the transformation of *Escherichia coli* are also described in this manual.

The composition of readily available nutrient media such as LB or TY media are also given in the manual by Sambrook et al.

EXAMPLE 1
Production of a genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) I.B.R. and partially cleaved with the restriction enzyme Sau3AI (Amersham Pharmacia, Freiburg, Germany, product description Sau3AI, Code no. 27-0913-02). The DNA fragments were desphosphorylated with shrimp alkaline phosphatase (Roche Diagnostics GmbH, Mannheim, Germany, product description SAP, Code no. 1758250). The DNA of the cosmid vector Super-Cos1 (Wahl et al. (1987) Proceedings of the National Academy of Sciences USA 84:2160–2164 I.B.R.), obtained from Stratagene (La Jolla, USA, product description Super-Cos1 Cosmid Vector Kit, Code no. 251301) was cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, product description BamHI, Code no. 27-0868-04). The cosmid DNA treated in this way was mixed with the treated ATCC13032-DNA and the batch was treated with T4-DNA ligase (Amersham Pharmacia, Freiburg, Germany, product description T4-DN ligase, Code no. 27-0870-04). The ligation mixture was then packed into phages using the Gigapack II XL Packing Extracts (Stratagene, La Jolla, USA, product description Gigapack II XL Packing Extract, Code no. 200217).

For the infection of the *E. coli* strain NM554 (Raleigh et al. 1988, Nucleic Acid Research 16:1563–1575 I.B.R.) the cells were taken up in 10 mM $MgSO_4$ and mixed with an aliquot of the phage suspension. Infection and titration of the cosmid library were carried out as described by Sambrook et al. (1989, Molecular Cloning: A Laboratory Manual, Cold Spring Harbor I.B.R.), the cells having been plated out on LB agar (Lennox, 1955, Virology, 1:190 I.B.R.) with 100 mg/l ampicillin. Recombinant individual clones were selected after incubation overnight at 37° C.

EXAMPLE 2
Isolation and Sequencing of the sigD Gene

The cosmid DNA of an individual colony was isolated using the Qiaprep Spin Miniprep Kit (Product No. 27106, Qiagen, Hilden, Germany) according to the manufacturer's instructions and partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Diagnostics GmbH, Mannheim, Germany, product description SAP, Product No. 1758250). After gel electrophoresis separation, the cosmid fragments were isolated in an order of magnitude of 1500 to 2000 bp using the QiaExII Gel Extraction Kit (Product No. 20021, Qiagen, Hilden, Germany).

The DNA of the sequencing vector pZero-1, obtained from Invitrogen (Groningen, Netherlands, product description Zero Background Cloning Kit, Product No. K2500-01), was cleaved with the restriction enzyme BamHI (Amersham Pharmacia, Freiburg, Germany, product description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor I.B.R.), the DNA mixture having been incubated overnight with T4 ligase (Pharmacia Biotech, Freiburg, Germany). This ligation mixture was then electroporated (Tauch et al. 1994, FEMS Microbiol Letters, 123:343-7 I.B.R.) into the *E. coli* strain DH5αMCR (Grant, 1990, Proceedings of the National Academy of Sciences U.S.A., 87:4645–4649 I.B.R.) and plated out onto LB agar (Lennox, 1955, Virology, 1:190 I.B.R.) with 50 mg/l zeocin.

The plasmid preparation of the recombinant clone was performed with the Biorobot 9600 (Product No. 900200, Qiagen, Hilden, Germany). The sequencing was carried out according to the dideoxy chain termination method of Sanger et al. (1977, Proceedings of the National Academy of Sciences U.S.A., 74:5463–5467 I.B.R.) as modified by Zimmermann et al. (1990, Nucleic Acids Research, 18:1067 I.B.R.). The "RR dRhodamin Terminator Cycle Sequencing Kit" of PE Applied Biosystems (Product No. 403044, Weiterstadt, Germany) was used. The gel electrophoresis separation and analysis of the sequencing reaction was carried out in a "rotiphoresis NF acrylamide/bisacrylamide" gel (29:1) (Product No. A124.1, Roth, Karlsruhe, Germany) using the "ABI Prism 377" sequencing apparatus from PE Applied Biosystems (Weiterstadt, Germany).

The raw sequencing data obtained were then processed using the Staden program package (1986, Nucleic Acids Research, 14:217–231 I.B.R.) Version 97-0. The individual sequences of the pZerol derivatives were assembled into a coherent contig. The computer-assisted coding region analysis was prepared using the XNIP program (Staden, 1986, Nucleic Acids Research, 14:217–231 I.B.R.).

The nucleotide sequence obtained is shown in SEQ ID No. 1. The analysis of the nucleotide sequence revealed an open reading frame of 567 base pairs, which was termed the sigD gene. The sigD gene codes for a protein of 188 amino acids.

This application claims priority to German Priority Document Application No. 100 43 331.6, filed on Sep. 2, 2000. The German Priority Document is hereby incorporated by reference in its entirety.

We claim:

1. A method for the preparation of L-amino acids, comprising:
culturing coryneform bacteria, which include an overexpressed sigD gene having a polynucleotide sequence which encodes the amino aid sequence of SE ID NO: 2, in a medium suitable for the expression of the sigD to thereby produce L-amino acids, wherein overexpression is achieved by increasing the copy number of said polynucleotide or by operably linking a promoter to said gene.

2. The method according to claim 1, further comprising isolating the L-amino acids.

3. The method according to claim 1, wherein said increased copy number is achieved by transforming said coryneform bacteria with a plasmid vector which comprises a nucleotide sequence which encodes the amino acid sequence of SEQ ID NO: 2.

4. The method according to claim 1, wherein the coryneform bacteria produce L-lysine.

5. The method according to claim 1, wherein the bacteria are *Corynebacterium glutamicum*.

6. A process for the preparation of L-amino acids, comprising culturing a coryneform bacterium which comprises an overexpressed polynucleotide comprising the nucleotides 301 to 864 of SEQ ID NO: 1, in a medium suitable for the expression of a sigD gene to thereby produce L-amino acids, wherein overexpression is achieved by transforming said bacteria with a vector comprising said polynucleotide.

7. The method according to claim 6, wherein the bacteria being fermented comprise, at the same time, one or more genes which are overexpressed; wherein the one or more genes is/are selected from the group consisting of:

a gene which encodes dihydrodipicolinate synthase,
a gene which encodes glyceraldehyde-3-phosphate dehydrogenase,
a gene which encodes triosephosphate isomerase,
a gene which encodes 3-phosphoglycerate kinase,
a gene which encodes glucose-6-phosphate dehydrogenase,
a gene which encodes pyruvate carboxylase,
a gene which encodes malate-quinone-oxidoreductase,
a gene which encodes aspartate kinase,
a gene which encodes homoserine dehydrogenase, a gene which encodes threonine dehydratase, a gene which encodes acetohydroxy acid synthase, a gene which encodes dihydroxy acid dehydratase, and the *Coryneform glutamicum* a gene which encodes a Zwa1 protein.

8. The method according to claim 6, wherein the bacteria being fermented have expression of one or more genes endogenous to said bacteria being eliminated; wherein the one or more genes is/are selected from the group consisting of:

a gene which encodes phosphoenol pyruvate carboxykinase, a gene which encodes glucose-6-phosphate isomerase, and a gene which encodes pyruvate oxidase.

9. A method for the preparation of L-amino acids, comprising culturing coryneform bacteria which include an overexpressed sigD gene having the polynucleotide sequence of SEQ ID NO: 1, in a medium suitable for the expression of the sigD gene to thereby produce L-amino acids, wherein overexpression is achieved by increasing the copy number of said polynucleotide or by operably linking a promoter to said gene.

10. The method according to claim 9, further comprising isolating the L-amino acid.

11. The method according to claim 9, wherein overexpression is achieved by transforming said bacteria with a plasmid vector which comprises the nucleotide sequence of SEQ ID NO: 1.

12. The method according to claim 9, wherein the L-amino acids are lysine.

13. The method according to claim 9, wherein the bacteria are *Corynebacterium glutamicum*.

14. The method according to claim 9, wherein the bacteria being fermented comprise, at the same time, one or more genes which are overexpressed; wherein the one or more genes is/are selected from the group consisting of:

a gene which encodes dihydrodipicolinate synthase, a gene which encodes glyceraldehyde-3-phosphate dehydrogenase, a gene which encodes triosephosphate isomerase, a gene which encodes 3-phosphoglycerate kinase, a gene which encodes glucose-6-phosphate dehydrogenase, a gene which encodes pyruvate carboxylase, a gene which encodes malate-quinone-oxidoreductase, a gene which encodes a aspartate kinase, a gene which encodes homoserine dehydrogenase, a gene which encodes threonine dehydratase, a gene which encodes acetohydroxy acid synthase, a gene which encodes dihydroxy acid dehydratase, and the *Corynebacterium glutamicum* Zwa1 gene.

15. The method according to claim 9, wherein the bacteria being fermented have expression of one or more genes endogenous to said bacteria being eliminated; wherein the one or more genes is/are selected from the group consisting of:

a gene which encodes phosphoenol pyruvate carboxykinase, a gene which encodes glucose-6-phosphate isomerase, and a gene which encodes pyruvate oxidase.

16. A process for producing L-amino acids comprising:

a) culturing coryneform bacteria which comprise an overexpressed polynucleotide of SEQ ID NO: 1, in a medium suitable for expression of the sigD gene to thereby produce L-amino acids, wherein overexpression is achieved by transforming said bacteria with a vector comprising said polynucleotide; and b) isolating the L-amino acids.

17. The method according to claim 16, wherein the bacteria being fermented comprise, at the same time, one or more genes which are overexpressed; wherein the one or more genes is/are selected from the group consisting of:

a gene which encodes dihydrodipicolinate synthase, a gene which encodes glyceraldehyde-3-phosphate dehydrogenase, a gene which encodes triosephosphate isomerase, a gene which encodes 3-phosphoglycerate kinase, a gene which encodes glucose-6-phosphate dehydrogenase, a gene which encodes pyruvate carboxylase, a gene which encodes malate-quinone-oxidoreductase, a gene which encodes aspartate kinase, a gene which encodes homoserine dehydrogenase, a gene which encodes threonine dehydratase, a gene which encodes acetohydroxy acid synthase, a gene which encodes dihydroxy acid dehydratase, and the *Corynebacterium glutamicum* Zwa1 gene.

18. The method according to claim 16, wherein the bacteria being fermented have expression of one or more genes endogenous to said bacteria being eliminated; wherein the one or more genes is/are selected from the group consisting of:

a gene which encodes phosphoenol pyruvate carboxykinase, a gene which encodes glucose-6-phosphate isomerase, and a gene which encodes pyruvate oxidase.

* * * * *